(12) United States Patent
McCombie et al.

(10) Patent No.: US 7,674,231 B2
(45) Date of Patent: Mar. 9, 2010

(54) WEARABLE PULSE WAVE VELOCITY BLOOD PRESSURE SENSOR AND METHODS OF CALIBRATION THEREOF

(75) Inventors: Devin B. McCombie, Medford, MA (US); Andrew T. Reisner, Newton, MA (US); Haruhiko H. Asada, Lincoln, MA (US); Phillip Shaltis, Attleboro Falls, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 11/840,654

(22) Filed: Aug. 17, 2007

(65) Prior Publication Data

US 2008/0039731 A1   Feb. 14, 2008

Related U.S. Application Data

(63) Continuation-in-part of application No. 11/508,123, filed on Aug. 22, 2006.

(60) Provisional application No. 60/710,085, filed on Aug. 22, 2005, provisional application No. 60/822,832, filed on Aug. 18, 2006.

(51) Int. Cl.
  *A61B 5/02* (2006.01)
(52) U.S. Cl. .............. 600/485; 600/481; 600/500; 600/504
(58) Field of Classification Search ......... 600/485–490, 600/500, 323, 509, 481, 504
  See application file for complete search history.

(56) References Cited

U.S. PATENT DOCUMENTS

| 4,524,777 | A |   | 6/1985  | Kisioka et al. | 128/677 |
| 4,846,189 | A |   | 7/1989  | Sun            | 600/492 |
| 4,869,262 | A | * | 9/1989  | Orr et al.     | 600/485 |
| 5,099,853 | A |   | 3/1992  | Uemura et al.  | 128/679 |
| 5,111,826 | A |   | 5/1992  | Nasiff         | 128/672 |
| 5,152,297 | A | * | 10/1992 | Meister et al. | 600/485 |
| 5,183,051 | A | * | 2/1993  | Kraidin et al. | 600/500 |

(Continued)

FOREIGN PATENT DOCUMENTS

WO   WO 98/04182   2/1998

(Continued)

OTHER PUBLICATIONS

Asada et al., "Mobile Monitoring with Wearable Photoplethysmographic Biosensors," IEEE Engineering in Medicine and Biology Magazine, vol. 22(3), pp. 28-40, May/Jun. 2003.

(Continued)

*Primary Examiner*—Patricia C Mallari
(74) *Attorney, Agent, or Firm*—Sunstein Kann Murphy & Timbers LLP (57) ABSTRACT

An apparatus and methods for performing a circulatory measurement on an extremity, such as a hand, of a subject. The circulatory measurement results in the derivation of an output circulatory metric that may encompass blood pressure or various other circulatory metrics. An indicator of an input circulatory metric at a locus on the extremity is measured, such as a pulse transit time, and calibrated to account for the hydrostatic component of blood pressure arising due to vertical displacement of the extremity with respect to the heart.

14 Claims, 6 Drawing Sheets

U.S. PATENT DOCUMENTS

| | | | | |
|---|---|---|---|---|
| 5,309,916 | A * | 5/1994 | Hatschek | 600/485 |
| 5,533,511 | A * | 7/1996 | Kaspari et al. | 600/485 |
| 5,778,879 | A | 7/1998 | Ota et al. | 128/672 |
| 5,995,859 | A * | 11/1999 | Takahashi | 600/323 |
| 6,280,390 | B1 * | 8/2001 | Akselrod et al. | 600/485 |
| 6,309,359 | B1 | 10/2001 | Whitt et al. | 600/507 |
| 6,322,515 | B1 | 11/2001 | Goor et al. | 600/485 |
| 6,537,225 | B1 * | 3/2003 | Mills | 600/481 |
| 6,547,741 | B2 | 4/2003 | Mori et al. | 600/490 |
| 6,592,528 | B2 * | 7/2003 | Amano | 600/485 |
| 6,932,772 | B2 * | 8/2005 | Kan | 600/490 |
| 7,014,611 | B1 | 3/2006 | Geddes et al. | 600/490 |
| 7,214,193 | B2 | 5/2007 | Freund et al. | 600/490 |
| 7,238,159 | B2 | 7/2007 | Banet et al. | 600/485 |
| 2002/0169381 | A1 * | 11/2002 | Asada et al. | 600/485 |
| 2002/0177781 | A1 * | 11/2002 | Amano | 600/485 |
| 2004/0024326 | A1 | 2/2004 | Yeo et al. | 600/500 |
| 2004/0162493 | A1 | 8/2004 | Mills | 600/481 |
| 2005/0096557 | A1 * | 5/2005 | Vosburgh et al. | 600/509 |
| 2005/0215912 | A1 | 9/2005 | Freund et al. | 600/485 |
| 2006/0074322 | A1 * | 4/2006 | Nitzan | 600/485 |
| 2006/0195034 | A1 * | 8/2006 | Skrabal et al. | 600/485 |

FOREIGN PATENT DOCUMENTS

| | | |
|---|---|---|
| WO | WO 98/25511 | 6/1998 |
| WO | WO 03/039326 | 5/2003 |

OTHER PUBLICATIONS

Shaltis et al., "*A Hydrostatic Pressure Approach to Cuffless Blood Pressure Monitoring*," 2004 26th Annual International Conference of the IEEE/EMBS, San Francisco, CA, USA, Sep. 1-5, 2004.

Shaltis et al., "*Calibration of the Photoplethysmogram to Arterial Blood Pressure: Capabilities and Limitations for Continuous Pressure Monitoring*," 2005 27th Annual International Conference of the IEEE/EMBS, Shanghai, China, Sep. 1-4, 2005.

Asada et al., "*Towards the Development of Wearable Blood Pressure Sensors: A Photo-Plethysmograph Approach*," Mini-Symposium, 2005 27th Annual International Conference of the IEEE/EMBS, Shanghai, China, Sep. 1-4, 2005.

Shaltis et al., "*Novel Design for a Wearable, Rapidly-Deployable, Wireless Noninvasive Triage Sensor*," 2005 27th Annual International Conference of the IEEE/EMBS, Shanghai, China, Sep. 1-4, 2005.

Reisner et al., "*A Miniaturized Device Capable of Near-Imperceptible Function: Toward a Wearable Monitor for Continuous Arterial Blood Pressure*," 2006 MGH Scientific Advisory Committee Research Symposium, Feb. 17, 2006.

Shaltis et al., "*Wearable, Cuff-less PPG-Based Blood Pressure Monitor with Novel Height Sensor*," 2006 28th Annual International Conference of the IEEE/EMBS, New York, New York, Aug. 30-Sep. 3, 2006.

Penaz, J., "*Photoelectric Measurement of Blood Pressure, Volume and Flow in the Finger*," Digest of the $10^{th}$ International Conference on Medical and Biological Engineering, Session 7, p. 104, 1973.

Teng et al., "*Continuous and Noninvasive Estimation of Arterial Blood Pressure Using a Photoplethysmographic Approach*," Proceedings of the $25^{th}$ Annual International Conference of the IEEE EMBS, pp. 3153-3156, Sep. 17-21, 2003.

Kamakoshi et al., "*Current Developments in non-invasive measurement of arterial blood pressure*," J. Biomed. Eng. vol. 10, pp. 130-137, Apr. 1988.

Kamakoshi et al., "*Long-term ambulatory monitoring of indirect arterial blood pressure using a volume-oscillometric method*," Med. & Biol. Eng. & Comput., vol. 23, pp. 459-465, 1985.

International Search Report, dated Jan. 19, 2007; received Jan. 23, 2007; PCT/US2006/032601.

International Search Report, dated Apr. 4, 2007; received Apr. 17, 2007; PCT/US2006/045590.

O'Rourke (ed.), "*Properties of the arterial wall: theory*", McDonald's Blood Flow in Arteries: Theoretical Experimental & Clinical Principles, Oxford U. Press, pp. 54-72, 1997.

USPTO, Office Action dated Dec. 8, 2008 in corresponding U.S. Appl. No. 11/508,123.

Nasser, Robert L., "Office Action", dated Jun. 3, 2009, U.S. Appl. No. 11/508,123.

John Allen and Alan Murray, Modelling the relationship between peripheral blood pressure and blood volume pulses using linear and neural network system identification techniques; Physiol. Meas. 20 (1999) 287-301. Printed in the UK.

* cited by examiner

WEARABLE PULSE WAVE VELOCITY BLOOD PRESSURE SENSOR AND METHODS OF CALIBRATION THEREOF

The present application is a continuation-in-part of U.S. patent application Ser. No. 11/508,123, filed Aug. 22, 2006, and, like that application, claims the priority of U.S. Provisional Patent Application Ser. No. 60/710,085, filed Aug. 22, 2005. Additionally, the present application claims the priority of U.S. Provisional Patent Application Ser. No. 60/822,832, filed Aug. 18, 2006. All of the foregoing applications are incorporated herein by reference.

TECHNICAL FIELD

The present invention relates to methods and apparatus for measuring arterial blood pressure at an extremity of a subject, and more particularly, to methods and apparatus based upon wave velocity measured between the locations of two photoplethysmographic sensors disposed on an extremity of a subject.

BACKGROUND OF INVENTION

It is well recognized that ambulatory blood pressure (BP) monitoring by means of wearable sensors has the potential to enable new levels of health-related vigilance and medical care in a number of novel settings, including, for example, controlling chronic hypertension and monitoring in-patients during convalescence. However, a significant challenge to realizing true non-invasive blood pressure (NIBP) measurement remains the problem of accounting for the unknown tension in the underlying arterial wall: If one simply measures pressure external to an artery (for instance, on the overlying skin), one is measuring the balance of intra-arterial pressure and the rapidly varying arterial wall tension. Ideal NIBP methods solve the problem of estimating intra-arterial wall pressures independently of the arterial wall tension. Yet, there is no optimal solution to truly wearable NIBP measurement. The ideal wearable device would be lightweight, easy-to-apply, non-invasive, small, unobtrusive, and as close to imperceptible as a regular wrist-watch or piece of jewelry. Existing NIBP measurement modalities, summarized as follows, have failed to meet the foregoing desiderata.

Oscillometric NIBP: The most common form of NIBP measurement, both in the home and in the clinical arena, uses the well-established oscillometric method. Oscillometry is based on the following principle: when the external cuff pressure equals the internal arterial pressure, the magnitude of arterial volume pulsations is maximal (because of the mechanical properties of arteries). While they are the standard-of-care, such devices nonetheless have shortcomings, including: (i) their circumferential compression of the extremity is uncomfortable, causing bruising or interrupting sleep; (ii) they are very susceptible to motion, since motion artifact cannot be distinguished from arterial volume pulsations, (iii) they are not readily miniaturizable so the device tends to be bulky, and (iv) overall, their accuracy versus a gold-standard is often inadequate. A more convenient version of the oscillometric cuff fits on the wrist, but measurement errors can arise if (v) the wrist is at a different vertical level from the heart, or (vi) if the patient has distal arterial fixed occlusions or vasospasm.

The Vasotrac Device and "Reverse Oscillometry": MedWave's BP sensor places a small "balloon" over the radial artery, increases the external pressure applied to the underlying radial artery, and measures the volumetric pulsations in the "balloon." It is therefore a variation of standard oscillometry, and the company describes the methods as "reverse oscillometry." The device is unsuitable for ambulatory monitoring because of its size and power requirements, moreover, it is motion-sensitive, like other oscillometric methods.

The Volume Clamp Method: The Portapres®/Finometer® family of devices of Finapres Medical Systems enables non-invasive measurement of BP waveform from a finger using photoplethysmographic (PPG) technology. In numerous instances, published works may refer to this measurement modality as 'photoplethysmography', although such usage is imprecise, and it can leave the incorrect impression that the PPG and arterial blood pressure (ABP) signals are interchangeable. The device is attractive in that it offers a non-invasive, continuous BP digital artery measurement, and it offers an umbilical cord mechanism to correct for hydrostatic offset errors (relative to the heart). Yet it requires a bulky, power-thirsty actuation system to drive the pneumatic cuff. Moreover, it circumferentially constricts the finger and prevents venous flow. Within minutes, this can become very uncomfortable, so much so that the Portapres comes equipped with two different finger cuffs so that it can alternate its operation between two fingers to minimize this discomfort.

The Finapres uses the volume clamp method of Penaz, which is based on the following insight: if a PPG signal is not changing, neither is the arterial transmural pressure, and visa-versa. Using an extremely rapid servo system with a finger cuff actuator, the Finapres adjusts the pressure in a finger cuff to keep a reference PPG signal flat throughout systole and diastole; the method is thus known as the 'volume-clamp' since the finger's blood volume is held constant. The waveform of whatever cuff pressure is necessary to keep the PPG signal flat must be equal and opposite to the digital arterial ABP.

Pulse Wave Velocity: Pulse wave velocity (PWV), the speed at which a pulse is transmitted through the arterial tree, is a function of arterial blood pressure, and there has been extensive academic and commercial effort to use this as a monitoring modality. The modality is described, for example, by Young et al, J Clin Monitoring 1995. However, according to Chen, Med Biol Eng. Comput. (2000), "No one has succeeded in realizing a reliable blood pressure monitor when only the pulse wave velocity or pulse arrival time is used." There are several reasons for these difficulties:

In addition to systolic BP and diastolic BP, PWV is also a function of the subject's vascular physiologic state.

Furthermore, PWV is also a function of the frequency content of their pulse waveform.

Raising and lowering the arms changes the hydrostatic pressure within the extremity, so PWV may be unreliable in any position except supine.

In a canine study, PWV was found to remain constant for all mean BP's below 100 mmHg. So PWV may not correlate with BP for individuals close to, or less than, the normotensive range (e.g. it may be difficult to detect over-medication, or monitor heart failure patients, with PWV).

PWV is distance divided by pulse transit time, but it is difficult to measure the distance accurately, or keep the distance constant.

To measure pulse transit time, a proximal and distal measurement are necessary. But the electrocardiogram (ECG) is a problematic marker of pulse onset, perhaps in part because of variable electromechanical delays. The fact that PPG measurements require the use of two distinct PPG sensors has also proven problematic.

Arterial tonometer solutions: Tonometers are very difficult to use, even in controlled laboratory conditions, and thus they have no role in ambulatory blood pressure measurement. Applanation tonometry requires that the artery wall segment be perfectly flat and that the pressure sensor overlies only the flattened portion of the artery and not extend over the curved portion of the artery. In this configuration, the flat segment of the arterial wall is unable to affect the balance between the intra-arterial pressure and the external tonometer pressure. These conditions are so difficult to achieve in practice that the one commercially available tonometer comes with a separate oscillometric cuff to calibrate the unreliable (in terms of absolute arterial pressure) tonometer unit.

Volume plethysmographs, e.g. Empirical Technologies wrist sensor: These devices can be light-weight and low powered. However, a plethysmograph, which is a volume signal, is quite different from the pressure signal. The volume of pulsation is a complex function of the arterial pressure, the mechanical properties of the artery, and the pressure applied by the sensor.

Wireless implanted devices e.g. CardioMEMS Enclosure: Technology now exists to implant an arterial pressure sensor for long-term pressure monitoring. However, in most instances a non-invasive device is preferable, and much more attractive to the broad population, than an implanted option.

SUMMARY OF INVENTION

In accordance with preferred embodiments of the present invention, a method is provided for deriving an output circulatory metric at an extremity of a subject.

As used herein, and in any appended claims, the term "circulatory metric" is used to encompass any parameter associated with blood circulation, including, without limitation, such quantities as blood pressure, its gradients and propagation, local blood volume, volume changes, flow velocity, etc.

Methods, in accordance with the invention, include:

measuring an input circulatory metric at a locus on the extremity;

measuring an indicator of a hydrostatic component of blood pressure associated with the locus on the extremity; and applying a calibration such as to provide the output circulatory metric based at least on the input circulatory metric and the indicator of the hydrostatic component of blood pressure.

In alternate embodiments of the invention, the output circulatory metric may be an arterial blood pressure of the subject, and, more particularly, at least one of systolic, diastolic, and mean arterial blood pressure.

In various embodiments of the invention, the step of measuring an input circulator metric may include:

measuring a first plethysmographic signal at a first position on the extremity of the subject;

measuring a second plethysmographic signal at a second position on the extremity of the subject, the second position characterized by a distance between the first position and the second position; and calculating a transit time of a circulatory pressure wave based on the first and second plethysmographic signals.

Additionally, a wave speed may be derived based on the calculated transit time and the distance between the first and second positions.

The first position may be at a wrist of the subject, and the first plethysmographic signal may be based upon measurement of blood volume in an ulnar artery of the subject or a radial artery of the subject. The second plethysmographic signal may be based upon measurement of blood volume in a digit of the subject.

In yet further embodiments of the invention, the step of measuring first and second plethysmographic signals may include obtaining circulatory waveforms at the first and second positions on the extremity and may have a further step of identifying a point of comparison between the waveform of the first plethysmographic signal and the waveform of the second plethysmographic signal. That point of comparison may be identified by defining a measure based on a specified fraction of the range between a maximum value of the waveform and a minimum value of the waveform.

In alternate embodiments of the invention, the calibration to provide the circulatory metric based at least on a derived wave speed may include identifying a response function of a sensor signal as a function of intra-arterial pressure, including the application of adaptive noise cancellation. There may be an additional step of obtaining the calibration, which may include identifying a value of pulse transit time at zero pressure that is independent of cardiovascular state. Additionally, a value may be measured that is related to the derivative of pulse velocity with respect to arterial pressure.

In accordance with another aspect of the invention, an apparatus is provided for performing a circulatory measurement on an extremity of a subject. The apparatus has a first plethysmographic sensor disposed at a first position on the extremity of the subject as well as a second plethysmographic sensor disposed at a second position on the extremity of the subject, wherein the second position is characterized by a distance with respect to the first position. The apparatus also has a processor for obtaining the circulatory measurement based on a derived transit time and the distance between the first and second positions and a calibration and a calibration relating the circulatory measurement to the derived wave speed.

In accordance with other embodiments of the invention, the first position may be at a wrist of the subject, and the first plethysmographic sensor may be adapted to measure blood volume in an ulnar artery of the subject or in a radial artery of the subject. The second plethysmographic sensor may be adapted for measuring blood volume in a digit of the subject.

BRIEF DESCRIPTION OF THE DRAWINGS

Advantages of the present invention and its several improvements will be seen when the following detailed description is read in conjunction with the attached drawings. These drawings are intended to provide a better understanding of the present invention, but they are in no way intended to limit the scope of the invention.

DETAILED DESCRIPTION OF PREFERRED EMBODIMENTS

In accordance with preferred embodiments of the present invention, a novel wearable device is described for monitoring blood pressure. Blood pressure is one example of an output circulatory metric that is of great clinical value. One embodiment of the invention uses the well-established principle that pulse transmission time (PTT) in an artery depends on blood pressure. In this case, PTT is an example of an "input circulatory metric" that may more readily be obtained by measurement than the blood pressure, which is of greater clinical value. This approach is, in theory, appealing because it does not require any squeezing or other discomforts associated with typical cuff-based devices. Yet, in the past, PTT-based methods have proven less reliable than desirable because compliance (and, hence, PTT) in an artery also changes for reasons other than blood pressure, as discussed above.

As used herein, and in any appended claims, the term "blood pressure" shall be taken to refer to any measure thereof, for example, to systolic and/or mean and/or diastolic measures, or to the continuous record of blood pressure (BP) as a function of time.

Devices in accordance with the present invention may advantageously reduce the necessary hardware to a very compact form-factor which can be worn with the comfort of a wrist-watch. Furthermore, changes in height of the wearer's hand may be exploited to recalibrate the relationship between arterial pressure and PTT so that blood pressure can continuously and more reliably be estimated from PTT. This approach may advantageously enable long-term PTT monitoring of arterial blood pressure.

The following description refers to concepts discussed in O'Rourke (ed.), "McDonald's Blood Flow in Arteries: Theoretical, Experimental and Clinical Principles," pp. 54-72, Oxford University Press (1997), which is incorporated herein by reference.

Measurement of Pulse Wave Velocity

Device configurations, in accordance with preferred embodiments of the invention, are now described with reference to FIG. 1. As shown, peripheral pulse wave velocity measurements are obtained from two photoplethysmograph (PPG) sensors placed at spatially distinct locations along the same peripheral arterial branch of the vascular tree. The leading sensor, which is more proximal with respect to the heart along the arterial branch, measures the propagating arterial pulse wave prior to the lagging sensor which is located more distal along the arterial branch. Each PPG sensor provides a voltage output corresponding to the arterial circulatory waveform at that location.

Figure 1:
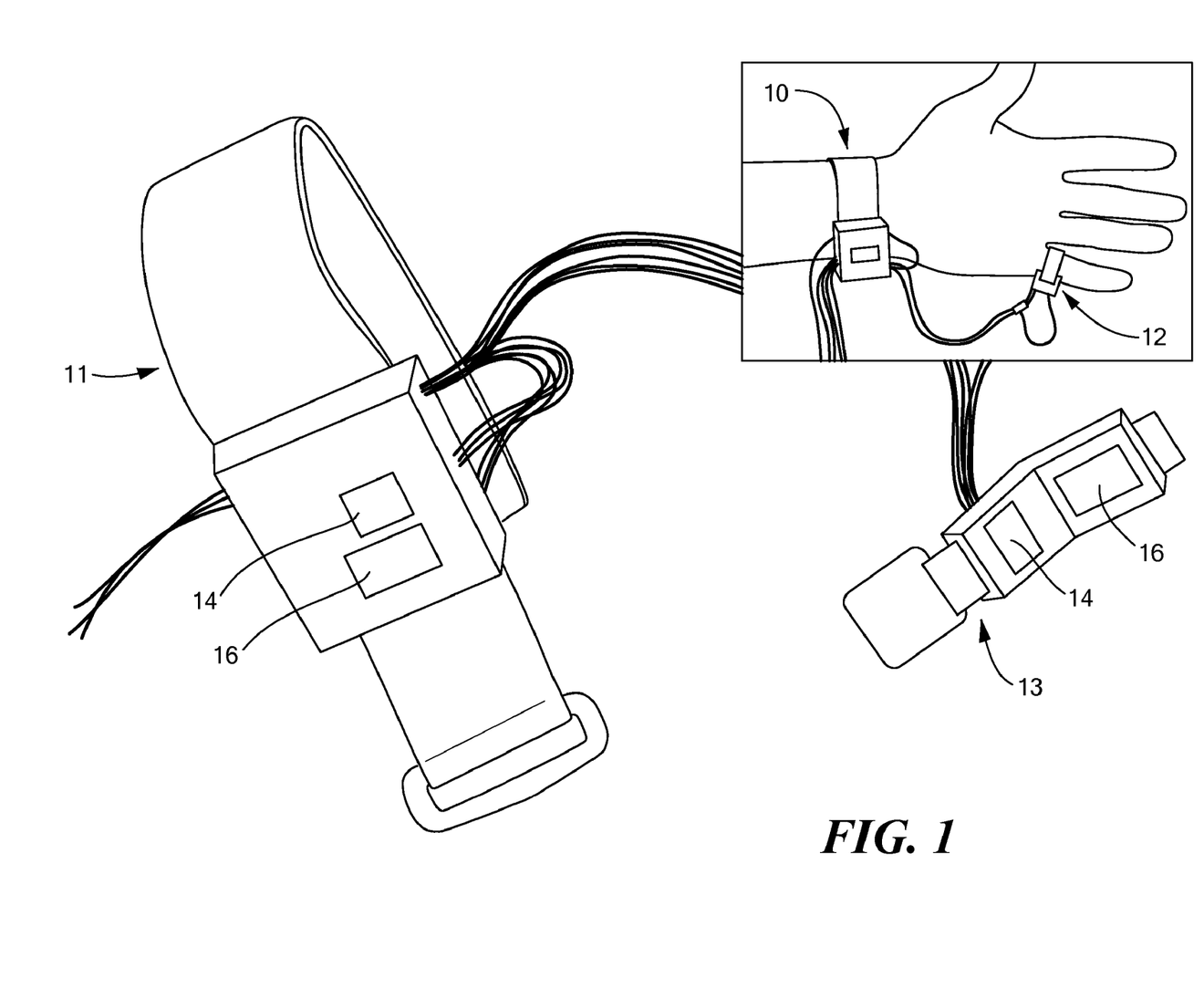
FIG. 1 shows one PPG sensor arrangement for measuring peripheral pulse wave velocity in accordance with an embodiment of the invention.

FIG. 1 shows components of a prototype of a particular embodiment in which the PPG sensors are configured such that a leading sensor 10 is directly above the ulnar artery at the wrist joint and a lagging sensor 12 is along the digital artery of the pinky finger.

In accordance with other embodiments of the invention, leading sensor 10 may be disposed on top of the radial artery at the wrist joint and lagging sensor 12 may be disposed along the digital artery of the index, or another, finger.

While the scope of the present invention is not limited to the configurations heretofore discussed, and further elaborated upon below, these configurations serve as examples for understanding the technique.

The pulse transit distance ($\Delta x$) between the two sensors is measured as the physical distance between the two sensors. Although this distance may differ slightly from the actual path length traversed by the propagating pressure wave it provides a very good approximation. This distance could be measured using a contact measurement device such as a caliper, or non-contact device that provides distance estimates using acoustic or optical sensors. In an alternative embodiment, the sensor can be constructed such that the distance between the leading and trailing sensor is reasonably constant and can be assumed to equal a known value.

Figure 2:
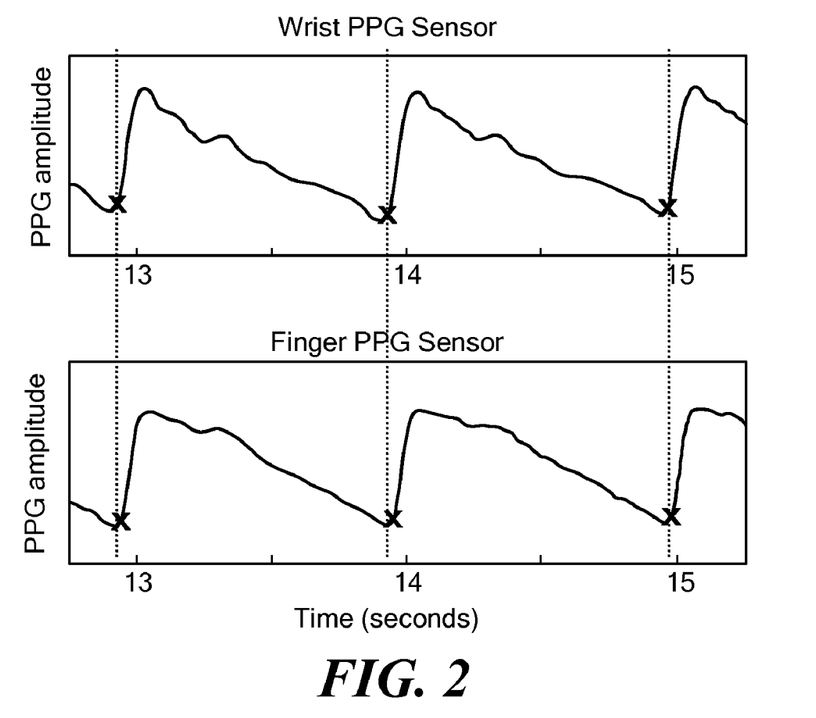
FIG. 2 depicts the estimation of pulse transit time using the difference in waveform onset time.

The transit time ($\Delta t$) between the two sensors of the propagating pressure wave is determined from the circulatory waveforms captured by the two in-line PPG sensors. Several techniques for estimating this transit time exist. These techniques include point-to-point type estimates that compare the difference in timing between corresponding features in the two measured waveforms, such as the difference between the onset time 20 of the pulse wave measured at lagging sensor 12 and the onset time 22 of the pulse wave at leading sensor 10 as shown in FIG. 2. Further discussion of the derivation of transit time measurements is provided below.

Within the scope of the invention, other integral type methods may also be used which make pulse transit time estimates based on longer periods of waveform data taken from the two sensors. Examples of this type of technique include estimation of the difference in time delay in the hemodynamics associated with two circulatory waveform signals using a system identification method such as a multi-channel blind system identification method.

The estimated peripheral pulse wave velocity c can then be determined from the measurements of pulse transit time $\Delta t$ and pulse transit distance $\Delta x$ as shown, according to:

$$c = (\Delta x)/(\Delta t). \tag{1}$$

The ability to utilize pulse wave velocity c to estimate arterial blood pressure P is based on the relationship that both the pulse wave velocity and arterial blood pressure shares with arterial vessel elasticity E.

The relationship between vessel elasticity and the wave speed of a pressure pulse in a thin walled vessel can be described by the Moens-Korteweg equation, $$c = \sqrt{\frac{Eh}{2R\rho}}. \tag{2}$$

The elasticity E of the vessel wall, in turn, exhibits a non-linear relationship with arterial blood pressure P and as such can be written as a function of pressure based on the equation described by Hughes et al.:

$$E = E_0 e^{\zeta P}. \quad (3)$$

Combining the previous two equations yields a relationship between pulse wave velocity and arterial blood pressure:

$$P = \frac{1}{\varsigma} \ln\left(\frac{2R\rho c^2}{hE_0}\right). \quad (4)$$

Other relationships based on different theoretical and/or empirical functional relationships may similarly provide the basis for calibration within the scope of the present invention.

Calibration of Pulse Wave Velocity to Arterial Blood Pressure

Calibration of the measured wave speed to the arterial pressure entails identifying a maximum of two different scalar terms according to Eqn. (4). Those two terms represent the scaling term on the natural logarithm ($k_1$) as well as a constant term ($k_1 * k_2$), where the arterial blood pressure is expressed phenomenologically as:

$$P = k_1(\ln(c^2) + k_2). \quad (5)$$

While calibration of the sensing apparatus will be described on the basis of an assumed functional relationship expressed in Eqn. (5), it is to be understood that the functional relationship of P as a function of c need not be constrained by a particular model within the scope of the present invention. More general functional dependences are explored below.

The value of $k_1$ can be estimated by measuring the effect that a change in peripheral arterial pressure ($\Delta P$) has on the measured peripheral wave speed. A change in peripheral arterial pressure may be achieved by altering the height ($h_s$) of the leading and lagging sensor relative to the height of the heart ($h_0$). By altering the height of the two sensors relative to the heart a measurable change in arterial pressure is produced which is equal to the hydrostatic pressure difference created by the difference in height between the heart and the sensors as in (6) where $\rho$ is the density of the blood which is assumed constant and g is the gravitational acceleration constant.

$$\Delta P = \rho g(h_s - h_0). \quad (6)$$

Using wave speed measurements taken at two distinct heights, along with knowledge of the difference in height between the two locations, provides for solution for the unknown constant, $k_1$ and for quantifying the slope of the pressure vs. natural log of the squared wave speed.

Methods for determination of height or differences in height are described in detail in pending U.S. patent application Ser. No. 11/508,123, filed Aug. 22, 2006, which is incorporated herein by reference. In some embodiments, a change in measured blood pressure, $\Delta BP$, may be correlated with an indicator of changes in hydrostatic component of the blood pressure via changes in height of the extremity. One method uses accelerometers to track the height of the extremity, allowing $\Delta BP$ to be estimated as a function of change in height, $\Delta h$, or change in hydrostatic pressure, $\Delta(\rho gh)$. In accordance with other embodiments, provided by way of example and without limitation, a fluid-filled catheter may be attached to the hand (the pressure at the base of the catheter will equal $\Delta(\rho gh)$, where h is the height of the catheter. Alternatively, the user may be asked to put his/her hand in known positions (e.g. straight in the air; over the heart; over the belly), and the height can be inferred within requisite precision of measurement.

The pressure vs. wave speed relationship for both sensor heights 1 and 2 are shown in (7a) and (7b) respectively, where it has been assumed that the only pressure difference between the two heights is due to the hydrostatic pressure difference.

$$P_1 = P + \rho g(h_{s,1} - h_0) = k_1(\ln(c_1^2) + k_2) \quad (7a)$$

$$P_2 = P + \rho g(h_{s,2} - h_0) = k_1(\ln(c_2^2) + k_2) \quad (7b)$$

A single difference equation can be formed by subtracting (7b) from (7a) as in (8) that produces a relationship between an easily estimated hydrostatic pressure change and the measured wave speed at the two heights.

$$P_1 - P_2 = \rho g(h_{s,1} - h_{s,2}) = k_1[\ln(c_1^2) - \ln(c_2^2)] \quad (8)$$

Thus, given measurements of wave speed at the two different heights and the difference in height between the two locations the constant $k_1$ can be calculated for any individual as in (9).

$$k_1 = \left(\frac{\rho g(h_{s,1} - h_{s,2})}{2\ln\left(\frac{c_1}{c_2}\right)}\right) \quad (9)$$

Determination of the second constant term $k_2$ in (5) depends on its variability across the population and/or for a given individual. Three potential scenarios exist for estimating this term. If the $k_2$ term shows very little variation across specific population subsets, which may be grouped according to age, sex, etc. than using a set of empirically predetermined $k_2$ terms may suffice for accurate pressure estimation. However, if large individual variation in $k_2$ does exist, then individual calibration will be required. If $k_2$ is relatively constant for an individual in different cardiovascular states than a single initial calibration for each state will be required. This initial calibration can be achieved using a diastolic pressure reading ($P_{cuff}$) from an oscillometric cuff along with corresponding estimates of wave speed from the onset times of the two circulatory waveforms and knowledge of $k_1$ as in (10). Once the initial calibration for the various states is achieved determination of $k_1$ alone should allow us to determine which previously identified $k_2$ is appropriate for the current pressure estimation.

$$k_2 = \left(\frac{1}{k_1}\right)P_{cuff} - \ln(c^2) \quad (10)$$

If the individual variability of $k_2$ is very large and this term spans a wide range of values, then $k_2$ requires estimation each time the two PPG sensors are attached to the patient and used for pressure estimation. Again, this calibration can be done using the pressure estimated from an oscillometric cuff and equation (10).

Although the use of an oscillometric cuff is one method of providing a known pressure to match with a given wave speed for estimating $k_2$, other methods for simultaneously providing both a single measurement of absolute pressure which along with the corresponding wave speed that can be used for calibration are within the scope of the present invention.

The Apparatus

The concept of estimating wave speed using this dual in-line PPG sensor method along with its ability to resolve wave speed changes given a hydrostatic pressure variation has been experimentally demonstrated.

Referring further to FIG. 1, each of the leading 10 and lagging 12 sensors comprises reflective-type PPG sensors, with a light-emitting diode (LED) 14 of wavelength at approximately λ=940 nm, and a photodetector 16, both enclosed within elastic cuffs 11 and 13 of adjustable bias pressure. The output of the PPG sensors is conditioned, such as with a standard analog band-limiting $2^{nd}$ order low-pass Butterworth filter ($F_c$=7000 Hz). Following acquisition of respective PPG waveforms, each sensor signal is digitally filtered, such as by use of a finite impulse response low-pass filter with a low-pass cutoff of approximately 20 Hz.

PPG waveform data are simultaneously collected from leading sensor 10 located along the ulnar artery at the wrist and from the lagging sensor 12 located along the digital artery of a finger as depicted in FIG. 1.

Within the scope of the present invention, both the radial and ulnar arteries may be used as possible locations for deriving a PPG signal, as may other positions on an extremity of the subject. PPG signals may be captured from both radial and ulnar arteries. The ulnar artery provides the following advantages:

- The ulnar artery permits a side-by-side LED-photodiode architecture, whereas a configuration in which the LED and photodiode are in-line with the artery, as appears to be necessary for a radial artery sensor, is less tolerant to misalignment than the side-by-side arrangement allowed by the ulnar artery.
- Side-by-side sensor architecture employed for an ulnar artery sensor is more comfortable under sensor loading pressures than the smaller surface area of an in-line architecture which is the type required by the radial artery.
- The area surrounding the ulnar artery is affected by movement of the little finger and ring finger, whereas the area surrounding the radial artery is affected by movement of the thumb, index finger, and middle finger. Sensing at the ulnar artery is thus less susceptible to motion artifact problems created by natural hand movement.
- A sensor housing placed above the ulnar artery allows natural motion of the wrist tendons and bones during rotation and flexion of the wrist.

Figure 4:
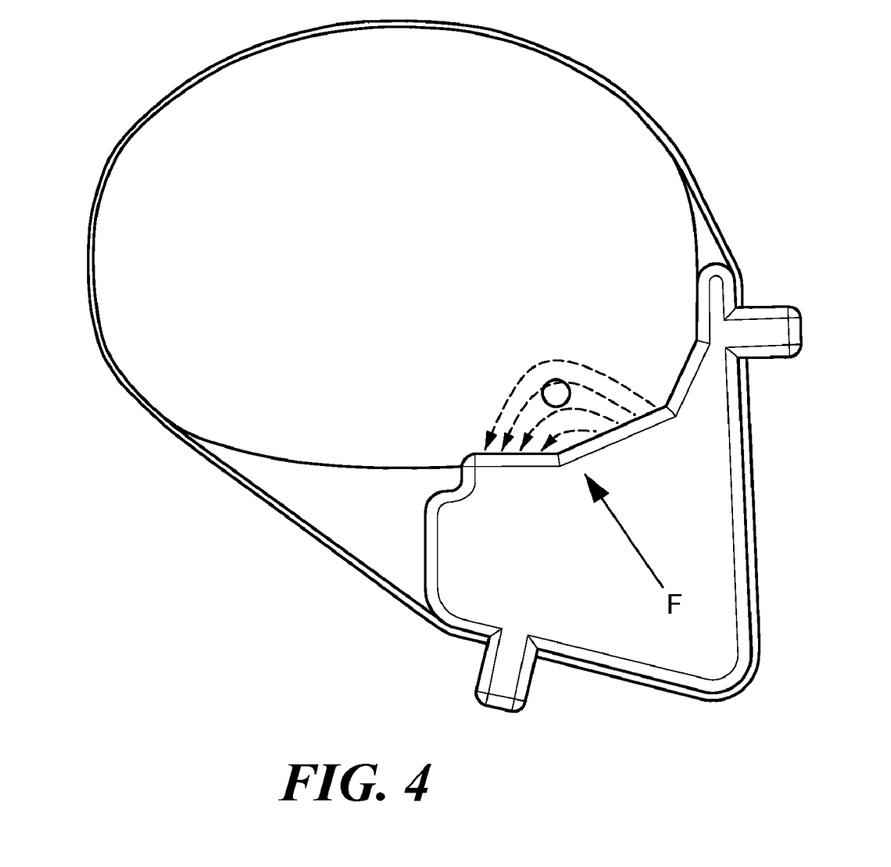
FIG. 4 depicts a geometry, in cross section, for an ulnar artery sensor housing, in accordance with embodiments of the present invention.

In addition to the arrangement of the LED and photodiode in the sensor housing, a key design issue in the wristwatch sensor is the external pressurization of the artery using a circumferential elastic band. In order to obtain a PPG signal with a sufficient signal-to-noise ratio, the tension in the elastic band is preferably adjusted to pressurize the sensor housing on the artery while minimizing patient discomfort. To achieve this goal the sensor housing was designed with an elevated angular contour as shown in FIG. 4 to translate the circumferential tension to ulnar artery pressurization.

Figure 5:
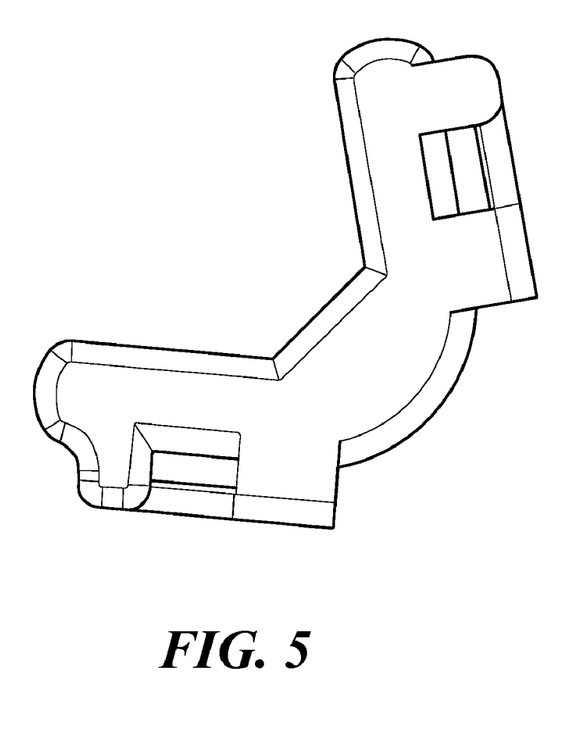
FIG. 5 depicts a geometry, in cross section, for an finger sensor housing, in accordance with embodiments of the present invention.

Lagging sensor 12 is preferably disposed, as discussed, on the little finger. A schematic of lagging sensor 12, which may be referred to herein as a "ring sensor," is provided in FIG. 5. The majority of the circuitry for the ring sensor may be located in the wristwatch sensor housing, providing for an advantageous size reduction of sensor 12. An advantage of this embodiment is that the difference in heights of the two sensors, relative, say, to the heart, is small and, in certain mathematical treatments, may be neglected.

For purposes of demonstration, the lower arm, wrist, and hand were held parallel to the horizontal plane and rested on a solid platform. The height of the two PPG sensors on the lower arm and hand was adjusted relative to the heart between three measured increments. The height difference between the three positions was 12 cm. Each height change corresponds to a change in hydrostatic pressure in the peripheral ulnar and digital artery (ΔP) of 8.8 mmHg. Approximately thirty seconds of PPG sensor data from the two sensors were collected and processed at each height. The data was processed using an algorithm to automatically detect the onset of each of the circulatory waveforms collected from the leading and lagging sensor.

Figure 3:
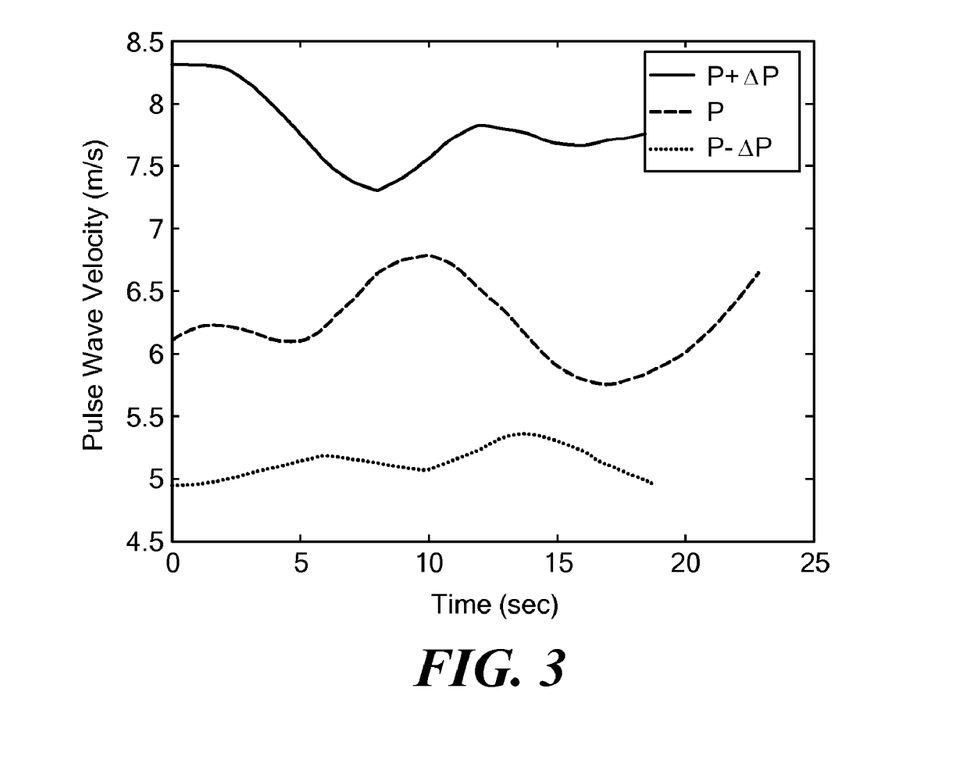
FIG. 3 is a plot of estimated peripheral wave speed under three sets of varying peripheral arterial pressure.

The distance (Δx) between the leading and lagging photodiodes was measured using a caliper and was found to be 134.04 mm. Peripheral pulse wave velocity measurement results at the three different heights were:

| Arterial Pressure | PWV Mean | PWV Std. Dev. |
|---|---|---|
| P + ΔP | 7.83 m/s | 0.43 m/s |
| P | 6.19 m/s | 0.45 m/s |
| P − ΔP | 5.11 m/s | 0.25 m/s | while experimental results, after applying a moving average filter over 4 estimated wave speeds, are displayed in FIG. 3 for each height.

It is to be understood that while the present discussion posits measurement of PWV using plethysmographs, other apparatus for measuring PWV is within the scope of the present invention. Such apparatus includes, but is not limited to the development of any signal related to arterial circulation, including pressure sensors (one or an array); photoplethysmographs (one or an array); bioimpedance measurements; or flowmeters (ultrasound or laser or otherwise). Similarly, pairs of sensors may be disposed at such combinations of extremity loci as wrist-nailbed, fingerbase-nailbed, forearm-wrist, or proximal arm—forearm.

Pulse Transit Time Estimation Using In-Line PPG Sensors

Measurement of the pulse transit time (PTT) between the wrist PPG sensor and the finger PPG sensor is derived from the circulatory waveforms measured at each location. Measurement of PTT is accomplished by computing the difference in the arrival times of a corresponding point of identity on each of the PPG waveforms.

A key difficulty in measuring PPT using PPG waveforms is the fact that the shape of the PPG waveform is a function of the transmural pressure acting across the artery at the sensor measurement site. The transmural pressure is the difference between the intra-arterial pressure and the external pressure being applied to the artery by the PPG sensor. The location of the point of identity on the PPG waveform used for PTT measurement is typically dependent on the shape of the waveform.

The intra-arterial pressure is composed of the hydrostatic pressure and the arterial pressure generated by the cardiac output of the heart. Therefore the shape of the waveform is a function of the applied sensor pressure, hydrostatic pressure, and arterial pressure.

Because the shape of the waveform depends on transmural pressure, identification of a point of comparison on the waveform (of the respective sensors) should, ideally, be largely independent of the shape. This requirement excludes techniques that rely on the slope or second derivative of the waveform. This requirement is increasingly important as the transit distance between the two sensors is made smaller.

Added to the effects of waveform shape on point selection, circuit noise in the PPG signal makes it difficult to select points of identity from certain portions of the PPG waveform during different phases of the cardiac cycle. In particular the rate of change of the PPG signal at the end of diastole and systole are very slow and the difference in amplitude of the sampled data points during these times are very small, much smaller than the amplitude of the circuit noise. Even after low-pass filtering the PPG signal selecting a point, and therefore a time of arrival in this region based on amplitude such as choosing the minimum point produces a large amount of variability in the estimated PTT. Thus, to reduce the variability produced by circuit noise a point on the rising edge of the PPG waveform during systole should be identified and selected when the rate of change and difference in point-to-point amplitude is greatest.

Accordingly, a novel method is now provided for determining a corresponding point of identity on each waveform for comparison that is largely independent of waveform shape and thus unaffected by changes in transmural pressure. Additionally, the point lies on the rising edge of the PPG waveform and estimates will be more robust to the circuit noise inherent in the PPG signal.

Figure 6:
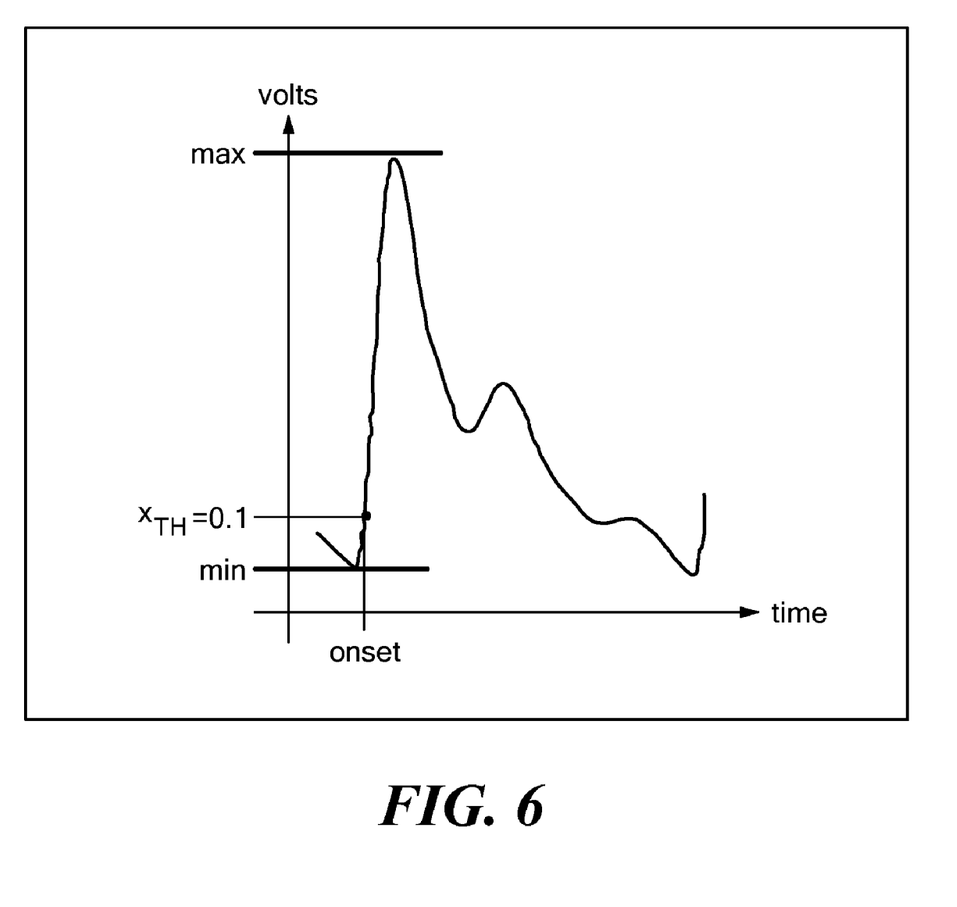
FIG. 6 depicts a typical waveform in connection with identification of a point of comparison in accordance with embodiments of the present invention.

A point of identity estimation technique based on a simple threshold principle is now described with reference to FIG. 6, with a point of identity determined on each waveform for every cardiac cycle. During each cardiac cycle a minimum voltage value is determined from the base of the waveform and a maximum voltage value is determined from the peak of the waveform, as shown in FIG. 6.

Although it is difficult to select a point in time corresponding to when the minimum and maximum values occur due to circuit noise, an approximate PPG voltage value can be found for these two features by finding an average value from a set of the most minimum and maximum values as shown in Eqns. (7) and (8).

$$\bar{y}_{min} = \frac{1}{L_{min}} \sum_{n=1}^{L_{min}} y_{min}[n] \quad (7)$$

$$\bar{y}_{max} = \frac{1}{L_{max}} \sum_{n=1}^{L_{max}} y_{max}[n] \quad (8)$$

Once these two values have been established for a particular cardiac cycle, a point of identity can be determined on the waveform using a predetermined threshold, $x_{TH}$, that lies on a scale of 0 to 1. In order to select the point of identity corresponding to the threshold the waveform must be re-scaled using the transformation described in (9).

$$x[n] = \left(\frac{1}{\bar{y}_{max} - \bar{y}_{min}}\right)(y[n] - \bar{y}_{min}) \quad (9)$$

The time of occurrence of the data point when the value of x[n] equals or surpasses $x_{TH}$ is selected as the time of the point of identity and used for comparison with the other PPG waveform.

However, the threshold method alone can not compensate for the changes in shape associated with transmural pressure change. It is the selection of the specific threshold level that allows this technique to be robust to such changes. In fact it is the character of the waveform itself that provides this robustness because the shape of the initial portion of the rising edge of the waveform is largely unaffected by changes in transmural pressure. Therefore if the threshold value is set to select a point of identity in the initial portion of the rising edge it should be unaffected by changes to the rest of the shape.

Experimental results suggest that a threshold, $x_{TH}$ of 0.1 or less will allow accurate PTT estimation that is independent of changes in waveform morphology, however the selection of any threshold value is within the scope of the present invention.

Moreover, it is to be understood that measurements of PTT based on other waveform indicia are within the scope of the present invention.

Calibration of Pulse Wave Velocity to Arterial Blood Pressure

Procedures used to determine the calibration equation relating pulse wave velocity and arterial blood pressure are now discussed in two sections: the first describing how the gain relating PTT and BP may be identified, and the second describing various methods for identifying the complete calibration equation relating pulse transit time measurements, or other indicators of blood flow, to blood pressure. Many other indicators of blood flow are known and commonly measured in the art, such as blood volume at a single locus, as measured by a plethysmograph, for example.

Figure 10:
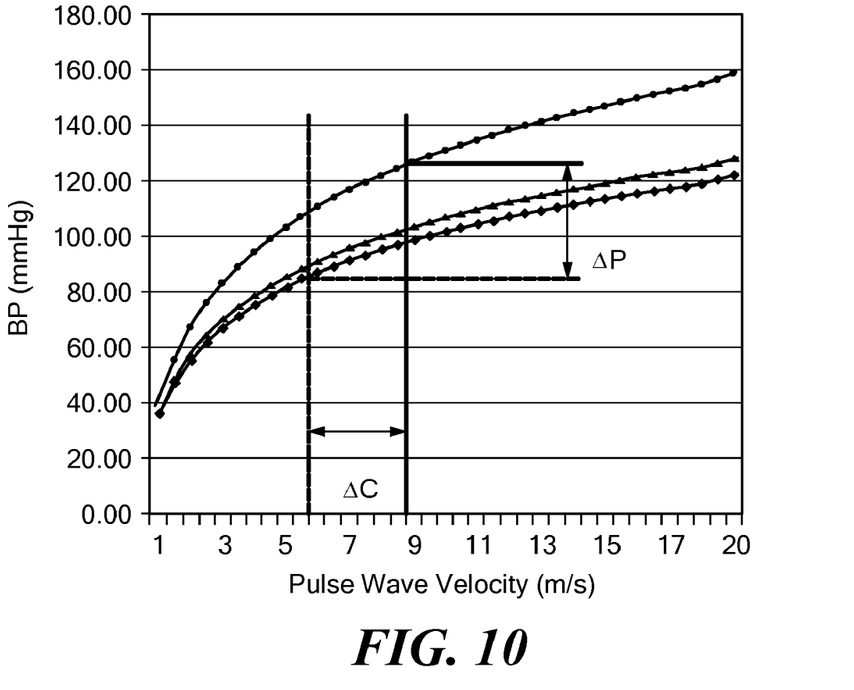
FIG. 10 shows three curves plotting pulse wave velocity vs. blood pressure under different subject states, in this case, before and after exercise.
Figure 11:
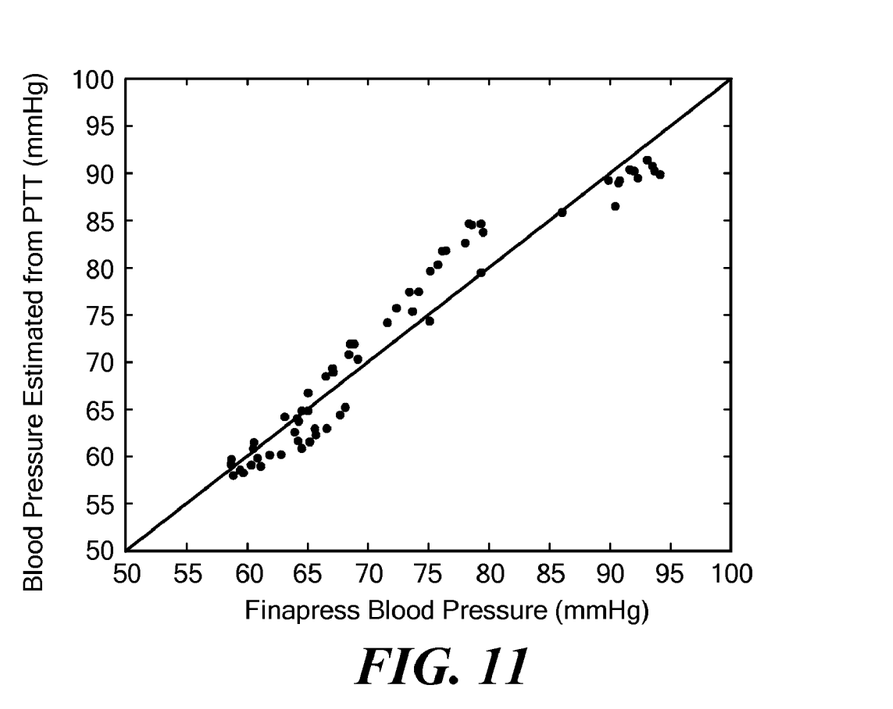
FIG. 11 shows a plot of blood pressure data estimated from the measured PTT data using the adaptive hydrostatic system identification (AHSI) parameters $\hat{k}_1$ and $\hat{y}_0$ compared to measured Finapres™ blood pressure data.

It is to be understood that particular functional relationships of BP to PTT may be assumed, over a particular range of PTT, including a locally linear relationship, or the quadratic relationship described above with respect to Eqn. (5). More general calibration curves are depicted in FIG. 10, where distinct curves of BP vs. PWV are shown for three states of a particular subject as determined before and after exercise.

A. Estimation of the PWV-to-BP Gain

Figure 7:
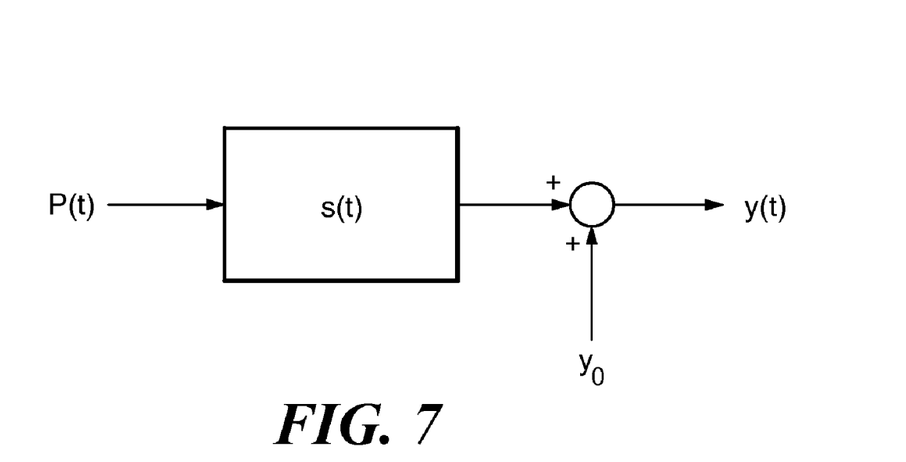
FIG. 7 schematically depicts the dynamic relationship between peripheral arterial blood pressure, P(t), and a measured non-invasive arterial sensor signal, y(t)

The dynamic relationship between peripheral arterial blood pressure, P(t) and a measured non-invasive arterial sensor signal, y(t) is shown in FIG. 7 where s(t) is the impulse response function of the sensor, that is to say, the function that, when convolved with a physiological input function yields the measured output function. The impulse response function represents the transduction dynamics of the sensor, while $y_0$ represents the steady state zero pressure sensor output.

Data derived from the sensor can be treated in analogy to data derived from a multi-channel system sharing common transduction dynamics by dividing it into distinct temporal segments as in Eqns. (10a) and (10b) for $\tau \leq t < t_{final}$.

$$P(t-\tau)*s(t)+y_0=y(t-\tau) \quad (10a)$$

$$P(t)*s(t)+y_0=y(t) \quad (10b)$$

By taking the difference between the forgoing equations, a differential relationship between the two temporal data sets can be formed as:

$$P(t)*s(t)-P(t-\tau)*s(t)=y(t)-y(t-\tau). \quad (11)$$

In the case of linear convolution, this expression can be further simplified using the distributive law:

$$[P(t)-P(t-\tau)]*s(t)=y(t)-y(t-\tau). \quad (12)$$

Intra-arterial hydrostatic pressure, $P_H(t)$ is described in (13) where ρ and g are as defined above, and where h(t)=0 is defined as the height at the level of the heart:

$$P_H(t)=\rho g h(t). \quad (13)$$

An additive model can be used to describe the contribution of hydrostatic pressure and the pressure contribution produced by arterial blood flow, $P_D(t)$ to total intra-arterial blood pressure, P(t), according to:

$$P(t)=P_D(t)+P_H(t). \quad (14)$$

This additive model can be substituted into the differential dynamic relationship described in (11) to produce an expression involving hydrostatic pressure as in (15) where $\Delta P_D(t) = P_D(t) - P_D(t-\tau)$, $\Delta h(t) = h(t) - h(t-\tau)$, and $\Delta y(t) = y(t) - y(t-\tau)$.

$$[\Delta P_D(t) + \rho g \Delta h(t)] * s(t) = \Delta y(t) \quad (15)$$

The goal of the hydrostatic calibration procedure is to identify the transduction dynamics, which, as stated, are manifest in the impulse response function s(t), insofar as it expresses the gain of the sensor in transducing the underlying intra-arterial pressure. The differential dynamic relationship in (15) consists of an unknown input pressure component $\Delta P_D(t)$ and a measurable hydrostatic pressure component $\rho g \Delta h(t)$. For an ideal periodic arterial flow input, and if $\tau$ is selected properly, $P_D(t) = P_D(t-\tau)$ and $\Delta P_D(t) = 0$. Therefore, we can identify s(t) directly from the intra-arterial hydrostatic pressure variation, $\rho g \Delta h(t)$ and the measured output $\Delta y(t)$.

The assumption of ideal periodicity is not generally valid because of the natural physiologic variation in peripheral arterial pressure across time, which is a result of a variety of sources including cardiac output variability, time varying periodic pressure waves produced by respiration and vasomotor activity, or other variation resulting from changes in sympathetic activity. Therefore, $\Delta P_D(t) \neq 0$ during the calibration period, $\tau \leq t \leq t_{final}$ and identification of s(t) from $\rho g \Delta h(t)$ using the expression in (15) requires a more sophisticated calibration algorithm.

One calibration algorithm that allows identification of s(t) from $\rho g \Delta h(t)$ despite the presence of an unknown pressure component $\Delta P_D(t)$ (for a suitably selected intra-arterial hydrostatic input) is based upon the principles of adaptive noise cancellation as now described.

For a linear system superposition allows us to separate the contributions of the two input components, $\Delta P_D(t)$ and $\rho g \Delta h(t)$, in our measured output $\Delta y(t)$ such that $\Delta y(t) = \Delta y_D(t) + \Delta y_H(t)$, following the definitions in (16a) and (16b).

$$\Delta P_D(t) * s(t) = \Delta y_D(t) \quad (16a)$$

$$\rho g \Delta h(t) * s(t) = \Delta y_H(t) \quad (16b)$$

Figure 8:
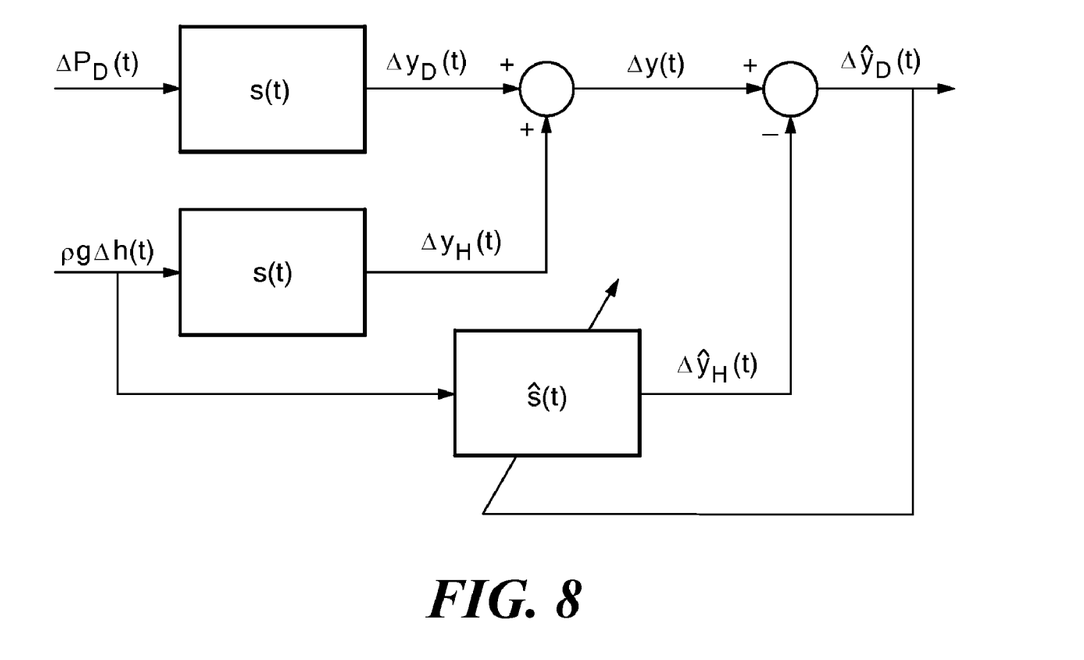
FIG. 8 is a block diagram depicting the fundamental structure of the adaptive hydrostatic blood pressure calibration algorithm in accordance with embodiments of the present invention.
Figure 9:
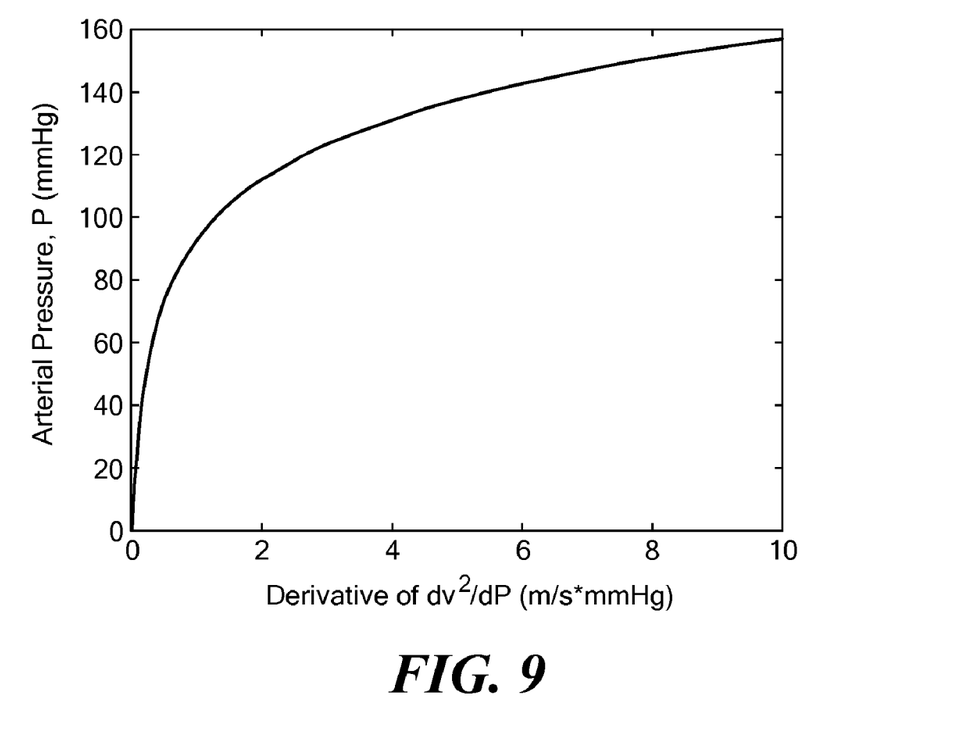
FIG. 9 is a plot of the relationship between pressure and the pressure derivative of pulse wave velocity, as discussed in the text.

The block diagram shown in FIG. 8 details the fundamental structure of the adaptive hydrostatic blood pressure calibration algorithm.

The square of the estimated signal $\Delta \hat{y}_D(t) = \Delta y(t) - \Delta \hat{y}_H(t)$ in FIG. 7. used to identify $\hat{s}(t)$. is shown in (17).

$$\Delta \hat{y}_D^2 = \Delta y_D^2 + (\Delta y_H - \Delta \hat{y}_H)^2 + 2\Delta y_D (\Delta y_H - \Delta \hat{y}_H) \quad (17)$$

Taking expectations of both sides of the equation in (17) leads to (18).

$$E[\Delta \hat{y}_D^2] = E[\Delta y_D^2 + (\Delta y_H - \Delta \hat{y}_H)^2 + 2\Delta y_D (\Delta y_H - \Delta \hat{y}_H)] \quad (18)$$

If the unknown arterial pressure change, $\Delta y_D(t)$ is uncorrelated with both $\Delta y_H(t)$ and $\Delta \hat{y}_H(t)$ than the expression in (18) can be reduced to:

$$E[\Delta \hat{y}_D^2] = E[\Delta y_D^2] + E[(\Delta y_H - \Delta \hat{y}_H)^2] \quad (19)$$

The signal power $E[\Delta y_D^2]$ is unaffected when minimizing $E[\Delta \hat{y}_D^2]$ by adjusting $\hat{s}(t)$ with respect to the $\rho g \Delta h(t)$ input, so that:

$$\min E[\Delta \hat{y}_D^2] = E[\Delta y_D^2] + \min E[(\Delta y_H - \Delta \hat{y}_H)^2] \quad (20)$$

When the transduction dynamics $\hat{s}(t)$ are adjusted to minimize $E[\Delta \hat{y}_D^2]$, then $E[(\Delta y_H - \Delta \hat{y}_H)^2]$ is also minimized providing a least squares estimate of $\Delta y_H(t)$. Therefore by designing $\rho g \Delta h(t)$ such that it is uncorrelated with $\Delta P_D(t)$ we can identify the sensor transduction dynamics $\hat{s}(t)$ by minimizing $([\Delta y(t) - \hat{s}(t) * \rho g \Delta h(t)])^2$ even for $\Delta P_D(t) \neq 0$.

Although the pseudo-random fluctuations in $\Delta y_D(t)$ are not subject to prediction, it is still possible to identify the periodic fluctuations in this parameter by observing the measured data $\Delta y(t)$ prior to calibration while holding $\rho g \Delta h(t)$ constant. By analyzing $\Delta y(t)$ in the frequency domain the primary frequency components can be determined and then a hydrostatic pressure input can be designed that is outside of these frequency bands.

Calibration of Pulse Wave Velocity to BP

This adaptive hydrostatic blood pressure calibration technique is readily applied to calibrate peripheral pulse wave velocity measurements v to peripheral arterial blood pressure P.

The functional PWV-to-BP relationship of Eqn. (23), of an exponential dependence on P, is readily derived by combining the Moens-Korteweg equation of Eqn. (21) with the expression modeling the nonlinear arterial stiffness (E) of Eqn. (22).

$$v = \sqrt{\frac{Ew}{2R\rho}} \quad (21)$$

$$E = E_0 \exp(\varsigma P) \quad (22)$$

$$v^2 = \left(\frac{E_0 w}{2R\rho}\right) \exp(\zeta P) \quad (23)$$

Under the assumption that the overall percent change in the arterial wall thickness, w and arterial radius, R are small over a physiologic pressure range, the squared velocity of Eqn. (23) can be expressed in terms of two constants, $k_1$ and $k_2$ as:

$$v^2 = (k_2) \exp(k_1 P). \quad (24)$$

The expression in (24) can simplified by observing that $$k_2 = v_0^2, \quad v = \left(\frac{\Delta x}{PTT}\right),$$

and $$v_0 = \left(\frac{\Delta x}{PTT_0}\right)$$

where $v_0$ and $PTT_0$ are respectively the steady state pulse wave velocity and pulse transit time at zero pressure. Taking the natural log of both sides of Eqn. (24), where $y(t) = \ln(PTT^{-2})$, $y_0 = \ln(PTT_0^{-2})$, one obtains:

$$\ln(PTT^{-2}(t)) = k_1 P(t) + \ln(PTT_0^{-2}). \quad (25)$$

The foregoing expression describes a simple linear, algebraic relationship between a measured variable and arterial pressure in which $\hat{k}_1$ can be identified using the adaptive algorithm described in the preceding section where P(t) is described by Eqn. (14) and the pressure underlying the site of PTT measurement can be adjusted hydrostatically. However, estimation of $PTT_0$ must thus be addressed, as discussed in the following section.

B. Full Calibration: Estimation of Pulse Transit Time at Zero Pressure ($PTT_0$)

Using the standard PTT-to-BP equations described in the immediately foregoing section, along with a known differential pressure input, does not allow identification of the full set of calibration parameters (specifically pulse transit time at zero pressure) necessary to estimate absolute blood pressure. In this section, various exemplary methods are taught for obtaining a full set of calibration parameters, thereby allowing absolute pressure estimation.

1) Cardiovascular State Invariant $PTT_0$

One method for estimating absolute pressure is to obtain an initial estimate of $PTT_0$ using an alternative snap-shot pressure estimation device such as an oscillimetric cuff and then adaptively identifying $k_1$ throughout the pressure estimation period using the hydrostatic identification method.

The assumption is that the value of $PPT_0$ is nearly constant across cardiovascular states and that the majority of change in the calibration equation can be captured by adaptively identifying $k_1$.

2) Alternative Calibration Equations

Another method for obtaining the full calibration equation relating pulse wave velocity to arterial blood pressure is to use an alternative model to represent the arterial wall compliance, such as the sigmoid pressure-volume model. Use of a more complex model structure prevents a cancellation of terms using the differential hydrostatic calibration methodology. Below, two alternative vessel wall compliance models are presented for describing the relationship between pulse wave velocity and arterial blood pressure. System identification of the model parameters using hydrostatic pressure change are also discussed.

The arterial wall compliance model derived from the sigmoid pressure-volume model is given by:

$$C = \frac{dV}{dP} = \frac{Ka\exp(-aP)}{(1+\exp(-aP))^2}. \tag{26}$$

Alternatively, the arterial wall compliance derived for an elastic tube under a distending pressure may also be given by:

$$C = \frac{dV}{dP} = \frac{2\pi R^3}{(Ehl - PR)}. \tag{27}$$

The Hughes model relating the modulus of elasticity of the arterial wall, E to arterial pressure ($E = E_0 \exp(\zeta P)$) can be incorporated into the expression in (27) to yield:

$$C = \frac{dV}{dP} = \frac{2\pi R^3}{(E_0 \exp(\zeta P) hL - PR)} \tag{28}$$

The Bramwell-Hill model can be used to describe the relationship between pulse wave velocity, v and arterial distensibility, $$v \frac{dP}{dV}$$

as:

$$v = \sqrt{\frac{1}{\rho} V \frac{dP}{dV}} \tag{29}$$

An expression relating pulse wave velocity and arterial pressure can be formulated for the sigmoid model by incorporating equation (26) into (29) along with the definition for volume in an elastic tube of unit length, $V = \pi R^2$, yielding:

$$v = \sqrt{\frac{\pi R^2 (1 + \exp(-aP))^2}{\rho K a \exp(-aP)}} \tag{30}$$

Similarly, an expression relating PWV and BP can be formed combining equation (28) with the definition of volume for an elastic tube into (29):

$$v = \sqrt{\left(\frac{E_0 h}{2\rho R}\right)\exp(\zeta P) - \left(\frac{1}{2\rho}\right)P}. \tag{31}$$

Assuming that the parameters in Eqns. (30) and (31) change very little across the physiologic pressure range, these two equations can be rewritten in terms of two different unknown constants as given by equation (32) and (33) for the sigmoid model and Hughes model, respectively:

$$v^2 = \frac{v_0^2}{4}\left(\frac{(1+\exp(-aP))^2}{\exp(-aP)}\right) \tag{32}$$

$$v^2 = v_0^2 \exp(k_1 P) - k_2 P \tag{33}$$

Alternatively, both of the foregoing expressions can be written in terms of pulse transit time where $$v = \frac{\Delta x}{PTT},$$

and $$v_0 = \frac{\Delta x}{PTT_0}$$

as:

$$PTT^{-2} = \frac{PTT_0^{-2}}{4}\left(\frac{(1+\exp(-aP))^2}{\exp(-aP)}\right) \quad (34)$$

$$PTT^{-2} = PTT_0^{-2}\exp(k_1 P) - k_3 P \quad (35)$$

These two different models expressing the relationship between pulse wave velocity/pulse transit time and blood pressure provide for solution for all the parameters in the equations using the differential hydrostatic pressure input with either a closed form solution (as is the case for Eqn. (34)) or an iterative non-linear optimization method.

These reformulations are useful for accurate parameter identification if the measured output is sensitive enough to the unknown parameters over the limited hydrostatic pressure range.

3) Derivative Estimation

Another method for providing full calibration is the use of the pressure derivative of pulse wave velocity, $$\frac{dv^2}{dP}.$$

This derivative is a measurable quantity and can be derived from pulse wave velocity data measured while providing very small changes in hydrostatic pressure.

This method requires the assumption that pulse wave velocity be a continuously smooth function of pressure and that the arterial compliance exhibits a maximum at zero pressure. The result of these two assumptions is that pulse wave velocity is a minimum at zero pressure and therefore the derivative of pulse wave velocity with respect to pressure is zero at a pressure equal to zero as given by:

$$\frac{dv^2(P=0)}{dP} = 0 \quad (35)$$

Using these assumptions, pressure can be defined as a function of the pulse wave velocity derivative as depicted graphically in FIG. 7 and as given by:

$$P = fcn\left(\theta, \frac{dv^2}{dP}\right) \quad (36)$$

While it is difficult to derive a closed form expression defining pressure, P, in terms of the derivative of pulse wave velocity, $$\frac{dv^2}{dP}$$

from first principles, an alternative approach is to find a set of basis functions, $$V_k\left(\frac{dv^2}{dP}\right)$$

which represent this function using the minimum number of parameters, L as in $$P\left(\frac{dv^2}{dP}\right) = fcn\left(\theta, \frac{dv^2}{dP}\right) \cong \sum_{k=0}^{L-1} b_k V_k\left(\frac{dv^2}{dP}\right). \quad (37)$$

Because the function relating pressure to the pressure derivative of pulse wave velocity is zero at zero pressure the constant term, $b_0$ in the basis would be equal to zero and we can solve for the remaining basis coefficients using a differential hydrostatic pressure measurement as in:

$$\Delta P = (P_1 - P_2) = \sum_{k=1}^{L-1} b_k \left(V_k\left(\frac{dv_1^2}{dP}\right) - V_k\left(\frac{dv_2^2}{dP}\right)\right) \quad (38)$$

Utilizing a basis function approximation may advantageously provide greater sensitivity of the output for the model coefficients and allow accurate identification and absolute pressure estimation. Note this method is applicable to the pressure derivative of $PPT^{-1}$ too.

Once the absolute pressure is estimated, the parameter, $PTT_0^{-2}$ in Eqn. (25) may be identified and then absolute pressure may be estimated without the use of the derivatives.

Demonstration of Operation

The onset time of every PPG pulse waveform measured in the ulnar artery ($T_U$) and the onset time of every PPG pulse waveform measured in the digital artery ($T_D$) were determined for a subject using the threshold detection method described in detail above, with onset detection threshold for both waveforms set at 2% ($x_{TH}$=0.02). Pulse transit time measurements were determined from the difference in onset times between the digital artery PPG and the ulnar artery PPG using the equation given by:

$$\begin{bmatrix} PTT(1) \\ PTT(2) \\ \vdots \\ PTT(N) \end{bmatrix} = \begin{bmatrix} T_D(1) \\ T_D(2) \\ \vdots \\ T_D(N) \end{bmatrix} - \begin{bmatrix} T_U(1) \\ T_U(2) \\ \vdots \\ T_U(N) \end{bmatrix}. \quad (33)$$

Only valid pulse transit time measurements were retained for identification and estimation. Valid pulse transit times were defined as those that were greater than zero and less than 80 milliseconds. This reduced the data sample size from N samples to M samples (M≦N). Invalid PPT estimates were generally the result of poor onset identification caused by noise in small amplitude PPG signals. The small amplitude PPG signals were the result of either sensor misalignment or insufficient sensor loading pressure.

A hydrostatic pressure measurement ($P_H$) was sampled from the full data set of hydrostatic measurements ($P_{H,Full}$) for each valid PTT measurement. The sample times for these hydrostatic measurements were set equal to the onset time of the digital artery PPG signal as given by:

$$P_H[m]=P_{H,Full}(^tT_D(m))\text{ for }m=1,2,\ldots,M. \tag{40}$$

Step 4: Adaptive Hydrostatic System ID

The adaptive hydrostatic system identification procedure described in section 4A was implemented to identify $\hat{k}_1$ using the data from step 3.

First, the measured PTT data can be transformed into the variable y(t) using the discrete time equation given by (35).

$$y[n] = \ln\left[\frac{1}{PTT^{-2}[n]}\right] \text{ for } n=1,2,\ldots,L \tag{35}$$

The next stage in the identification procedure is to divide both sets of measurements, y[n] and $P_H[n]$ into two equal sized data sets. The primary objective in dividing the data sets is to generate as rich a differential data set as possible. For our pseudo-periodic input this can be achieved by selecting τ in equation (4a) using the definition given by equation (36).

$$\tau = \left(\frac{1}{2F_{input}}\right) \tag{36}$$

In terms of our discrete PTT data it is more difficult to select a discrete number of samples that corresponds to a time period τ, due to the non-uniform sampling rate associated with our valid set of measurements. From an observation of the valid PPT data set the average number of samples ($N_{avg}$) contained in a time period equal to that described in (36) can be estimated. The measured differential output data set shown in FIG. 6 can be constructed from the measured output using the formula given by equation (37).

$$\Delta y[n]=y[n]-y[n-N_{avg}] \text{ for } n=(N_{avg}+1),(N_{avg}+2),\ldots,L \tag{37}$$

In a similar manner the differential hydrostatic pressure data set shown in FIG. 6 can be constructed from measured hydrostatic pressure samples using the formula given by equation (38).

$$\rho g\Delta h[n]=\Delta P_H[n]=P_H[n]-P_H[n-N_{avg}] \text{ for } n=(N_{avg}+1),(N_{avg}+2)\ldots,L \tag{38}$$

In FIG. 6 the estimated differential hydrostatic pressure contribution to the measured differential output $\Delta y[n]$ is given by (39).

$$\Delta\hat{y}_H[n]=\hat{k}_1\Delta P_H[n] \tag{39}$$

The unknown differential physiologic pressure contribution to the measured differential output $\Delta y[n]$ is given by (40).

$$\Delta\hat{y}_D[n]=\Delta y[n]-\Delta\hat{y}_H[n]=\Delta y[n]-\hat{k}_1\Delta P_H[n] \tag{40}$$

The adaptive hydrostatic pressure identification algorithm described in section 3 states that if $\Delta P_H[n]$ is uncorrelated with $\Delta P_D[n]$ than minimizing the expression given by (41) with respect to $\hat{k}_1$.

$$(\Delta y[n]-\hat{k}_1\Delta P_H[n])^2 \text{ for } n=(N_{avg}+1),\ldots,L \tag{41}$$

Is equivalent to minimizing the expression given by (42) with respect to $\hat{k}_1$.

$$(\Delta y_H[n]-\hat{k}_1\Delta P_H[n])^2 \text{ for } n=(N_{avg}+1),\ldots,L \tag{42}$$

Therefore, minimizing the squared error between the measured differential output and only the estimated differential hydrostatic output allow us to find the best least squares estimate of $\hat{k}_1$.

Blood pressure data were also derived from the blood pressure waveforms measured by the Finapres™. In addition to the adaptive hydrostatic system identification described above, the model coefficient $k_1$, was also identified using the measured Finapres™ pressure P[n] in the differential form given by $$\Delta P[n]=P[n]-P[n-N_{avg}] \text{ for } n=(N_{avg}+1),(N_{avg}+2),\ldots,L. \tag{49}$$

Both the transformed PTT data ($\Delta y[n]$) and transformed pressure data ($\Delta P[n]$) were used to identify $k_1$ by minimizing the expression given by (50).

$$(\Delta y[n]-\hat{k}_1\Delta P[n])^2 \text{ for } n=(N_{avg}+1),\ldots,L \tag{50}$$

Along with $k_1$, the second model parameter from equation (25), $\ln(PTT_0^{-2})$, which is defined as $y_0$, was identified by minimizing the expression given by equation (51) with respect to $y_0$ using the measured Finapres™ pressure data.

$$((y[n]-\hat{k}_1P[n])-\hat{y}_0)^2 \text{ for } n=1,2,\ldots,L \tag{51}$$

The final stage of the experimental implementation procedure combined the results derived from several of the previous steps to estimate blood pressure from the measured pulse transit time data.

Blood pressure estimation was performed using the model parameter $\hat{k}_1$ identified from the adaptive hydrostatic system identification (AHSI) algorithm along with the model parameter $\hat{y}_0$ identified using the Finapres™ blood pressure measurements. Blood pressure was estimated using the equation given by $$\hat{P}[n] = \left(\frac{1}{\hat{k}_1}\right)(y[n]-\hat{y}_0) \text{ for } n=1,2,\ldots,L. \tag{52}$$

Blood pressure data estimated from the measured PTT data using the AHSI parameters $\hat{k}_1$ and $\hat{y}_0$ are shown in FIG. 10 compared to the measured Finapres™ blood pressure data.

The described embodiments of the invention are intended to be merely exemplary and numerous variations and modifications will be apparent to those skilled in the art. In particular, blood characteristics other than arterial blood pressure may be measured employing the techniques described herein and is within the scope of the present invention. All such variations and modifications are intended to be within the scope of the present invention as defined in the appended claims.

We claim:

1. A method for deriving an output circulatory metric at an extremity of a subject, the method comprising:
   measuring a first plethysmographic signal at a first position on the extremity of the subject and measuring a second plethysmographic signal at a second position on the extremity of the subject, each of the signals being measured at a plurality of heights, by means of a sensor disposed on the extremity of the subject, the second position characterized by a distance between the first position and the second position;
   establishing a functional relationship using a digital computer, the functional relationship based at least on the measurements of the first and second plethysmographic signals at the plurality of heights, the functional relationship providing a quantitative relationship between the first and second plethysmographic signals and the output circulatory metric absent a direct measurement of the output circulatory metric at each of the plurality of heights; and calculating a transit time of a circulatory pressure wave based on the first and second plethysmographic signals;

deriving a wave speed based on the calculated transit time and the distance between the first and second positions; and applying the functional relationship to derive the output circulatory metric.

2. The method of claim 1, wherein the output circulatory metric is an arterial blood pressure of the subject.

3. The method of claim 2, wherein the arterial blood pressure of the subject is at least one of systolic, diastolic, and mean arterial blood pressure.

4. The method of claim 1, wherein the first position is at a wrist of the subject.

5. The method of claim 1, wherein the first plethysmographic signal is based upon measurement of blood volume in an ulnar artery of the subject.

6. The method of claim 1, wherein the first plethysmographic signal is based upon measurement of blood volume in a radial artery of the subject.

7. The method of claim 1, wherein the second plethysmographic signal is based upon measurement of blood volume in a digit of the subject.

8. The method of claim 1, wherein the step of measuring first and second plethysmographic signals include obtaining circulatory waveforms at the first and second positions on the extremity.

9. The method of claim 8, further comprising identifying a point of comparison between the waveform of the first plethysmographic signal and the waveform of the second plethysmographic signal.

10. The method of claim 8, wherein identifying a point of comparison includes defining a measure based on a specified fraction of the range between a maximum value of the waveform and a minimum value of the waveform.

11. The method of claim 1, wherein the step of establishing a functional relationship includes identifying a response function of a sensor signal as a function of intra-arterial pressure.

12. The method of claim 11, wherein the step of identifying a response function of the sensor signal as a function of intra-arterial pressure includes application of adaptive noise cancellation.

13. The method of claim 1, further comprising identifying a value of pulse transit time at zero pressure that is independent of the output circulatory metric.

14. The method of claim 13, further comprising measurement of a value related to a derivative of pulse velocity with respect to arterial pressure.

* * * * *